United States Patent [19]

Nielsen

[11] Patent Number: 5,129,726
[45] Date of Patent: Jul. 14, 1992

[54] APPARATUS FOR COLOR CONTROL OF OBJECTS

[76] Inventor: Bjarne C. Nielsen, Egegaardsvej 2, DK-6541 Bevtoft, Denmark

[21] Appl. No.: 488,002

[22] PCT Filed: Nov. 9, 1988

[86] PCT No.: PCT/DK88/00185
§ 371 Date: May 9, 1990
§ 102(e) Date: May 9, 1990

[87] PCT Pub. No.: WO89/04468
PCT Pub. Date: May 18, 1989

[30] Foreign Application Priority Data

Nov. 10, 1987 [DK] Denmark .............................. 5875/87

[51] Int. Cl.⁵ .......................... G01J 3/50; G01N 21/27
[52] U.S. Cl. .................................... 356/402; 356/400; 356/407; 356/425
[58] Field of Search ............... 356/402, 405, 406, 407, 356/416, 418, 419, 425, 446; 250/226

[56] References Cited

U.S. PATENT DOCUMENTS

| | | | |
|---|---|---|---|
| 4,131,540 | 12/1978 | Husome et al. | 209/582 |
| 4,171,909 | 10/1979 | Kramer et al. | 356/73 |
| 4,546,700 | 10/1985 | Kishner et al. | 101/211 |
| 4,647,211 | 3/1987 | Browne | 356/447 |
| 4,721,389 | 1/1988 | Dejaiffe | 356/445 |

FOREIGN PATENT DOCUMENTS

| | | |
|---|---|---|
| 1942746 | 2/1971 | Fed. Rep. of Germany . |
| 2633087 | 2/1977 | Fed. Rep. of Germany . |
| 3244286 | 5/1984 | Fed. Rep. of Germany . |
| 0080019 | 4/1986 | Japan .................................. 356/416 |
| 8203208 | 3/1984 | Netherlands ........................ 356/416 |
| 363902 | 11/1974 | Sweden . |
| 440401 | 7/1985 | Sweden . |
| 612760 | 8/1979 | Switzerland . |
| 655183 | 3/1986 | Switzerland . |
| 2066452 | 7/1981 | United Kingdom . |
| 2128732 | 5/1984 | United Kingdom . |

*Primary Examiner*—F. L. Evans
*Attorney, Agent, or Firm*—Fred A. Keire; David M. McConoughey

[57] ABSTRACT

An apparatus for color control of objects (11) has an approximately point-shaped light source in the form of a xenon flash lamp (16), which illuminates a specific, desired area through a diaphragm (17). Light reflected from the object is received by a detector unit (13) having three or more sensors (22) with their respective spectral sensitivities, which are positioned at such a great distance from the object that each receives substantially the same amount of light from all parts of the illuminated area. The detector signals are amplified by amplifiers adapted to filter all signals exhibiting another timewise variation than the light source, so that disturbing influence from the surroundings is avoided. The apparatus is simple and fast and is versatile in use.

6 Claims, 1 Drawing Sheet

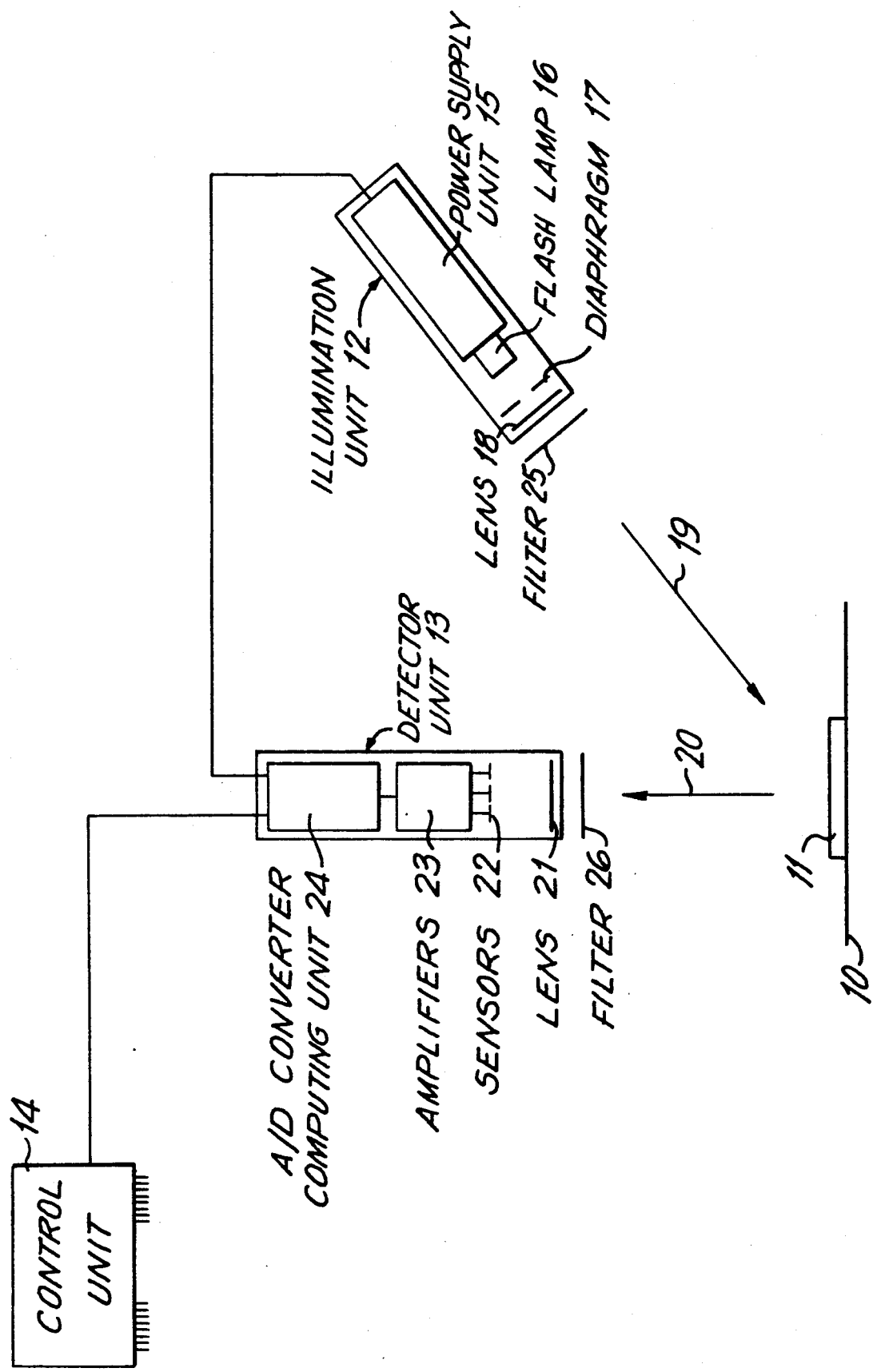

APPARATUS FOR COLOR CONTROL OF OBJECTS

The invention relates to an apparatus for colour control of an object, the apparatus containing a light source for illuminating the object and a detector for filtering and measuring the light reflected from the object.

In industrial colour control or colour sorting it is often necessary to control objects which move with a great velocity, have different sizes, are hot or wet or are difficult being into contact with colour control equipment for other reasons. It is therefore desirable that the colours of the objects can be controlled at a distance.

It is known, e.g. from German Patent DE 3 244 286 to perform colour control by illuminating an object with light from a pulsed source of light, whereupon the reflected light is detected. The reflected light is imaged through a lens system on a sensors of the detector unit. Since the light source is pulsed, light having another timewise variation may be filtered by suitable signal processing. The detected light is then compared with a reference signal from the pulsed object source, the colour of the light is determined.

CH 612.760 relates to an optical system, where an object is illuminated by obliquely incident light, and where the reflected light is collected by a lens system and passed to sensors through an optical fibre system.

It is a problem in colour measurement that the colour detectors have a finite light-sensitive area. The sensitivity in this area is constant for an ideal sensor, but in practice the sensitivity of the sensors can vary very strongly even within small distances of the light-sensitive area. This gives problems when an object point is imaged in an image point. Thus, the detected light intensity will depend upon the position of the object, where even small changes in the position of the object will entail that different light intensities are measured. Since known colour measuring devices, where the measurement takes place without contact between the object and the detector, mainly image the object on a plurality of sensors, it will be impossible to obtain a constant colour measurement when an object, e.g. a shrimp, passes through the measurement area on a conveyor belt, or if the measurement area is very large, e.g. 1 m². When imaging is performed on the sensors, a non-controllable, weighted averaging of the colour of the measurement area is effected. In addition, a lens system is to be trimmed to minimize the chromatic aberrations. To minimize these aberrations it is known to use an aperture diaphragm so that the used part of the lenses is limited, thus reducing the light intensity. For the measurement area to be imaged on, e.g. three detectors, the system must be strictly symmetrical.

Another problem associated with prior art apparatuses is that it is not possible to perform colour measurement where the object and the detector/light source are separated by a great distance. Thus, the close proximity of the detection/light source to the object in prior art apparatuses poses a cleaning problem when the colour of wet or dusty objects, e.g., fish, shell fish, chips, egg white, etc., on a conveyor belt is to be measured. Additionally, objects having different thicknesses pose problems if their mutual thickness variation is not small with respect to the measurement distance. Such a variation causes problems. In particular, in a system where the measurement is imaged on the sensors.

For objects to be conveyed with an even speed it is necessary to perform simultaneous colour measurements.

In the prior art it is often a problem that the useful wavelength range is small. This band limitation is caused by the fact that the known colour measuring apparatuses contain different sophisticated components whose losses are wavelength dependent, e.g. imaging components. Frequently, it may be advantageous to have a measurement range from 300 nm (ultra violet) to 2000 nm (infra red) at disposal.

Therefore, the object of the invention is to provide an apparatus which is capable of giving reproducible measurements of a colour of an object, irrespective of the objects' position in the measurement area. Further, the measurement must be contact-free and the representation of the colour of the object must be independent of variations in thickness.

Another object of the invention is to provide an apparatus which minimizes the number of optical components used. A further object of the invention is to provide a great measurement distance in order to vary the dimensions of the measurement area, advantageously from above 1 m² to below 1 mm². Yet another object of the invention is to provide an apparatus capable of making colour measurements far beyond the range of the visible spectrum.

These objects are achieved by an apparatus for measuring the average value of colour in a measurement area of an object, the apparatus comprising a light source for illuminating the object, the light source being adapted to illuminate the measurement area evenly and with great intensity, the measurement area comprising the part of the object the colour of which is to be measured; means for defining the measurement area, the means being interposed between the light source and the object; and a detector for measuring light reflected from the object, the detector including a plurality of sensors, each sensor having a field of vision containing the entire measurement area; wherein (i) the detector is located at a position such that each sensor image-free receives substantially the same amount of light from all parts of the measurement area and (ii) the average distance between the detector and all parts of the measurement area is greater than the variation in distance therebetween.

Means for defining the measurement area is interposed between the light source and the object and is only used for varying the size of the illuminated area. Such means includes, for example, a lens and a diaphragm. The diaphragm is a visual field diaphragm in contrast to the aperture diaphragms which are used in the prior art to improve the image quality. The colour then recorded by the sensors will thus be indicative of the average colour in the entire illuminated area. Since no imaging lens systems or the like are incorporated between the object and the detector, the apparatus is not sensitive to changes in the position of the object within the measurement area. Since the number of optical boundary faces is limited, the losses in the system are likewise limited. There are no substantial propagation losses between object and detector, which makes it possible to measure with a great distance between object and measuring equipment.

Objects having various sizes and irregular shapes (e.g., shrimp) can be measured when the objects are placed on a black background or when light falling outside the objects is otherwise prevented from reaching the detectors. These measurements will be reproducible and independent of where the objects are present in a measurement area, because all parts of the measurement area provide equal contributions to the colour representation formed by the detector.

The measurement area can be formed in any manner (e.g., by illuminating an object on a conveyor belt in a streak transverse to the conveyor belt), and the size of the object can be varied within a very large range. Since the size of the measurement area is adjusted solely by regulating the aperture of the light source, a simple and inexpensive optical system is obtained, where changing to new objects is performed merely by changing the aperture of the light source. Thus, in the case of visual inspection, it is easy to change the size of the measurement area while simultaneously checking whether the measurement area has moved, because the measurement area corresponds to the illuminated region.

Further, the apparatus is suitable for measuring an average value for objects having greatly varying colour patterns.

When the light source is a xenon flash lamp, means for defining the measurement area advantageously comprise a convex lens and a diaphragm which are interposed between the light source and the object to be illuminated such that the illumination can be limited to just the desired measurement area which may have an arbitrary, desirable form.

Advantageously, the apparatus according to the invention includes means for filtering signal contributions from the surroundings. In a preferred embodiment, the detector contains amplifiers for amplification of electric signals, each of which signals represents the light passed through a colour selective element, which amplifiers are adapted to filter the signal contributions originating from light having a time-wise variation which is different than that of the illumination pulses.

In another embodiment, the invention is directed to a method for measuring a dimension of an object in a specific direction which method comprises illuminating the object in a streak in the direction and measuring the light reflected from the object with an apparatus according to the invention. The reflected light intensity measured by the detector of the apparatus is a measure of the dimension, e.g., width, of the object in the beam direction.

If the dimensional measurement in accordance with the invention is performed in a plurality of specific positions, the shape of the object can be determined. Thus, in another embodiment, the invention is directed to a method for determining the shape of an object. In accordance with this embodiment, the object can be positioned, for example, on a conveyor belt and the individual dimension measurements can be performed in predetermined positions on the conveyor belt.

In yet another embodiment of the invention, the apparatus includes means for eliminating light contributions from a specular surface of an object whose colour is to be determined. Means for eliminating light contributions from a specular surface comprises, for example, a first polarization filter having a first polarization direction and a second polarization filter having a second polarization direction, the first polarization filter being interposed between the light source and the object and the second polarization filter being interposed between the object and the detector. This arrangement of filters is capable of eliminating light contributions from a specular background because it is known that polarized light remains polarized after specular reflection, but is spread as diffuse light by a non-specular surface.

An embodiment of the apparatus of the invention is shown schematically in the drawing and will be described in more detail below with reference to this drawing.

In the drawing, 10 is a conveyor belt on which objects 11 to be colour controlled are conveyed. When an object arrives at the control position at an illumination unit 12 and a detector unit 13, a control unit 14 is informed that measurement is to take place. This information is passed on to the detector unit 13 and via this to the illumination unit 12. The latter has a power supply unit 15 with a trigger to trigger a xenon flash lamp 16, which forms an approximately point-shaped light source and emits a strong light pulse with a duration of 2-6 $\mu$s on reception of the signal from the control unit. This light passes through a visual field diaphragm 17 having a shape corresponding to the area of the object 11 whose colour is to be controlled and through a convex lens 18 which sends a bundle of substantially parallel rays 19 towards the object 11.

When the object is non-specular, it spreads diffuse light, and part of this light impinges on the detector unit 13 which has a lens 21 which sends the light towards three sensors 22 having different spectral sensitivities. The detector unit is positioned at such a great distance from the object that each sensor receives substantially the same amount of light from the various parts of the illuminated area from the object. The lens 21 may be omitted since it only serves as an amplifying element and does not serve as an imaging element. The detector does not satisfy the imaging equation, but is positioned considerably more closely to the lens than to the image point. The sensors may optionally each have their own colour filter (not shown). The signals from the sensors are amplified by amplifiers 23, which are adapted to only allow signals having the same timewise variation as the light source to pass, and the amplified analog signals are converted to digital signals in an A/D converter and a computing unit 24. The computing unit computes the colour and intensity of the light on the basis of the strength of the three signals, and the measurement result is compared with stored values corresponding to approved/rejected for the object in question. When sorting, the measurement results is compared with a plurality of stored limits, and the object is classified accordingly.

The object may also be fluorescent and be illuminated with excitation light with a specific wavelength through a colour filter.

The apparatus may be used for size determination by illumination of an area having at least the same size as the object. The measured intensity of light with the colour of the object is indicative of the size (area) of the object. If the object is placed on a background having a colour different from the object, the reliability of the size determination will be particularly great, it being possible to determine the intensity of light both with the colour of the object and with the colour of the background. This procedure is of particular importance if the colour is not quite constant from object to object.

When applying the system to width determination, The object is illuminated in a narrow streak transversely to the object. The measured intensity of light having the colour of the object is indicative of the width of the object.

Shape determination may be performed by positioning the object on a conveyor belt running past a width determining set-up as described above. Comparison of measurements of the width of the object with simultaneous measurements of the position of the conveyor belt provides an indication of the shape of the object. It may e.g. be determined in this way whether an ice-cream cone has its tip pointing forwardly or rearwardly on the conveyor belt, which is important in automatic packaging procedures.

When using a set of intersecting polarization filters 25, 26, placed at the illumination units and at the detector unit, respectively, the apparatus may be used for colour determination of objects present on a specular background, since specular light is completely suppressed by the polarization, while only 75% of diffuse light disappears. Similarly, undesirable reflections from wet glossy or otherwise specular surfaces are suppressed.

This set-up may also be used for detecting whether an impurity is present on a specular surface and for determining the colour of the impurity. What is in mind here is particular detection whether an egg white present in a stainless steel container is polluted with yolk or something else. When using the colour controlling properties of the apparatus it may be determined whether the impurity consists of yolk, blood or yolk string.

The shown and described apparatus may be modified in several ways within the scope of the invention. E.g., a modulated lamp, which may be a xenon lamp, may be used as a light source instead of a flash lamp.

I claim:

1. An apparatus for measuring the average value of colour in a measurement area of an object, said apparatus comprising:
    (a) a light source for illuminating said object, said light source being adapted to illuminate said measurement area evenly and with great intensity, said measurement area comprising the part of the object the colour of which is to be measured;
    (b) means for defining the measurement area, said means being interposed between said light source and said measurement area; and
    (c) a detector for measuring light reflected from said object, said detector including a plurality of sensors, each sensor having a field of vision containing the entire measurement area; wherein (i) the detector is located at a position such that each sensor image-free receives substantially the same amount of light from all parts of the measurement area and (ii) the average distance between the detector and all parts of the measurement area is substantially greater than the distance between the individual sensors.

2. An apparatus according to claim 1, wherein said light source is a xenon flash lamp and said means for defining said measurement area includes a convex lens and a diaphragm interposed between said xenon flash lamp and said object, said convex lens and said diaphragm limiting the illumination of the object so as to define the desired measurement area.

3. An apparatus according to claim 1, wherein said light source is illuminating the measurement area with pulses of short duration, said detector further includes filter means which filters out signal contributions originating from light having a time-wise variation which differs from the time-wise variation of light from the light source.

4. An apparatus according to claim 3, wherein said detector comprises amplifiers for amplification of signals from the sensors, said signals representing light passed through a colour selective element, said amplifiers filtering out signal contributions originating from light having a time-wise variation which differs from the time-wise variation of light from the light source and also which amplifies signals having the same time-wise variation as that of the light from the light source.

5. An apparatus according to claim 1, wherein said measurement area is partly specular and partly diffusing, and further including means for eliminating light contributions from said specular surface, said means being placed in the optical path between said light source and said detector.

6. An apparatus according to claim 5, wherein said means for eliminating light contributions from said specular surface comprises a first polarization filter having a first polarization direction and a second polarization filter having a second polarization direction, said first polarization filter being interposed between said light source and said object and said second polarization filter being interposed between said object and said detector.

* * * * *